United States Patent
Trebbi et al.

(10) Patent No.: US 8,613,584 B2
(45) Date of Patent: Dec. 24, 2013

(54) SYSTEM AND METHOD FOR TRANSFERRING AND MOVING ELEMENTS OF AN AUTOMATIC PACKING MACHINE

(75) Inventors: Claudio Trebbi, Medicina (IT); Alessandro Bisi, Argelato (IT); Francesco Sanmartin, Cornedo Vicentino (IT)

(73) Assignee: IMA Life S.R.L., Ozzano dell-Emilia (Bologna) (IT)

( * ) Notice: Subject to any disclaimer, the term of this patent is extended or adjusted under 35 U.S.C. 154(b) by 1362 days.

(21) Appl. No.: 12/296,155

(22) PCT Filed: Apr. 4, 2007

(86) PCT No.: PCT/IB2007/000895
§ 371 (c)(1),
(2), (4) Date: Dec. 29, 2008

(87) PCT Pub. No.: WO2007/113664
PCT Pub. Date: Oct. 11, 2007

(65) Prior Publication Data
US 2009/0202335 A1    Aug. 13, 2009

(30) Foreign Application Priority Data

Apr. 5, 2006 (IT) .............................. BO2006A0244

(51) Int. Cl.
*B65H 29/00* (2006.01)
*B23Q 3/00* (2006.01)

(52) U.S. Cl.
USPC ................. 414/788; 29/464; 29/466; 29/559; 29/281.4

(58) Field of Classification Search
USPC ................ 29/465, 466, 467, 468, 559, 281.4; 414/217, 402, 788
See application file for complete search history.

(56) References Cited

U.S. PATENT DOCUMENTS

| | | | |
|---|---|---|---|
| 5,364,219 | A | 11/1994 | Takahashi et al. |
| 5,622,470 | A | 4/1997 | Schaefer et al. |
| 6,089,812 | A | 7/2000 | Junker |
| 6,138,721 | A | 10/2000 | Bonora et al. |
| 6,524,052 | B1 | 2/2003 | Yamauchi et al. |
| 2003/0044261 | A1 | 3/2003 | Bonora et al. |
| 2004/0052624 | A1 | 3/2004 | Miyano et al. |

FOREIGN PATENT DOCUMENTS

| | | |
|---|---|---|
| EP | 0 858 948 | 8/1998 |
| EP | 1 170 209 | 1/2002 |
| EP | 1 170 213 | 1/2002 |
| EP | 1 561 473 | 8/2005 |
| EP | 1 598 275 | 11/2005 |
| WO | WO 92/12864 | 8/1992 |

OTHER PUBLICATIONS

International Search Report for PCT/IB2007/000885, mailed Feb. 14, 2008.
International Search Report for PCT/IB2007/000895, mailed Oct. 9, 2007.

*Primary Examiner* — Jermie Cozart
(74) *Attorney, Agent, or Firm* — Nixon & Vanderhye P.C.

(57) ABSTRACT

A system for transferring and moving elements removably associable with a packaging machine comprises at least a transferring unit provided with a movement arrangement suitable for receiving and supporting the elements, the movement arrangement being movable for transferring and/or removing the elements to and/or from the machine; a method for transferring and moving elements removably associable with a packaging machine provides supporting and conveying the elements using at least a transferring unit and transferring and/or removing the elements to and/or from the packaging machine using the movement arrangement of the transferring unit.

32 Claims, 5 Drawing Sheets

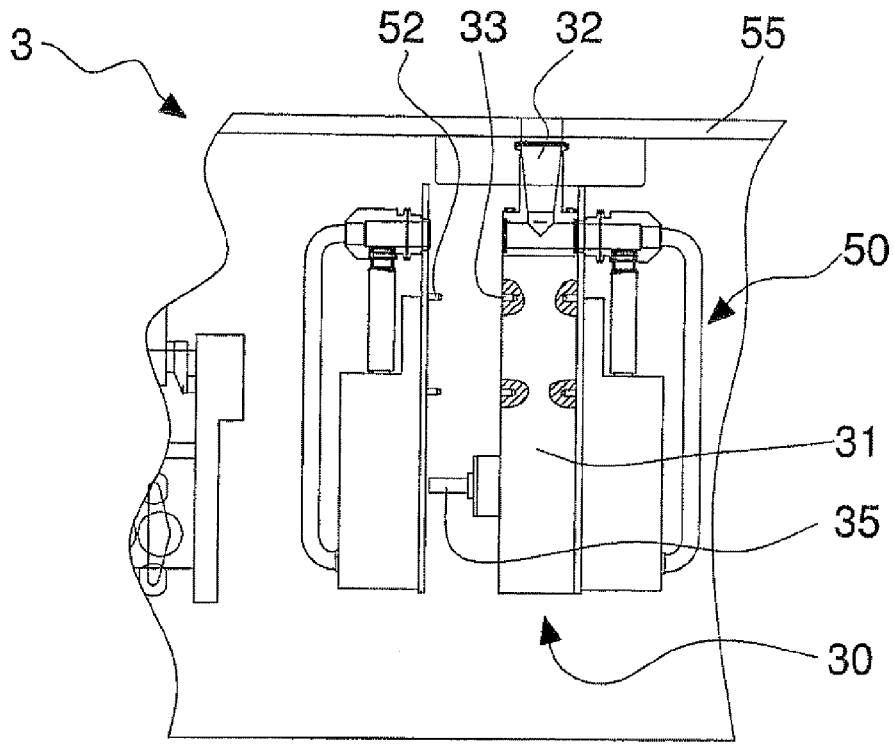
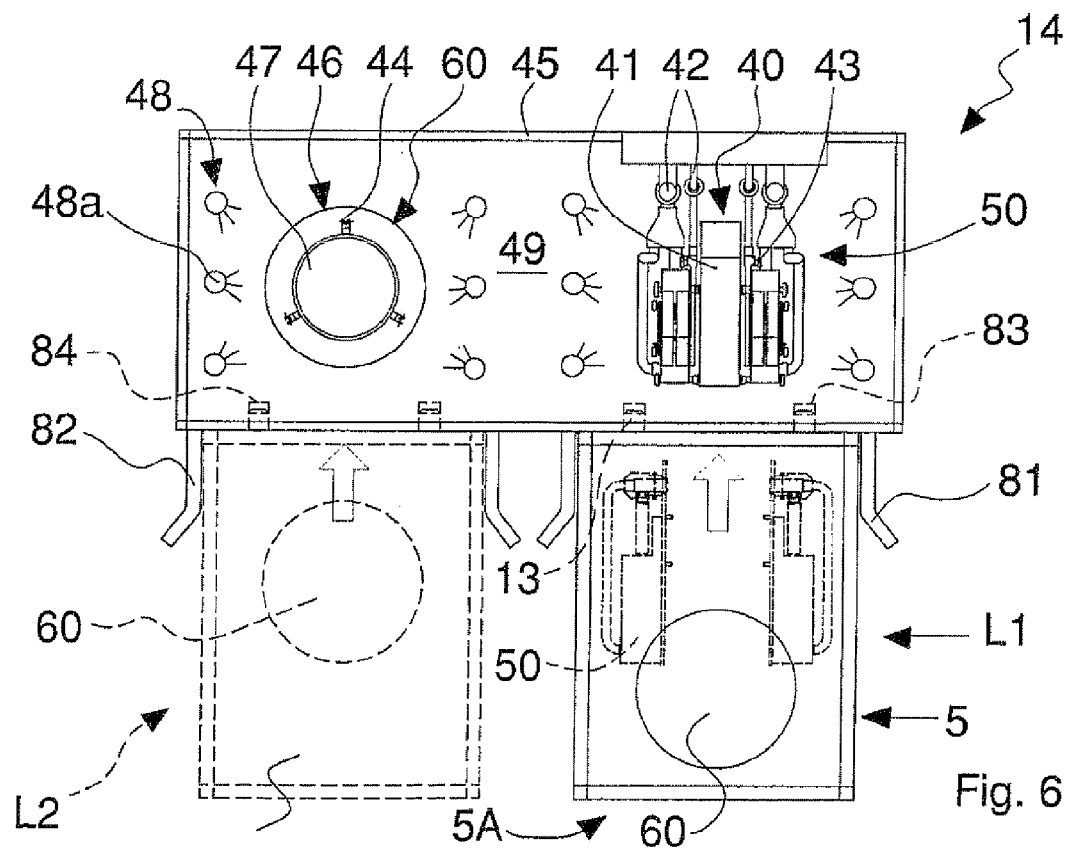

SYSTEM AND METHOD FOR TRANSFERRING AND MOVING ELEMENTS OF AN AUTOMATIC PACKING MACHINE

CROSS-REFERENCE TO RELATED APPLICATIONS

This application is the U.S. national phase of International Application No. PCT/IB2007/000895, filed 4 Apr. 2007, which designated the U.S. and claims priority to Italy Application No. BO2006A000244, filed 5 Apr. 2006, the entire contents of each application is hereby incorporated by reference.

BACKGROUND OF THE INVENTION

The present invention relates to a system and a method for transferring and moving elements of an automatic packaging machine.

In particular, the invention relates to a system and a method for performing a plurality of operations automatically or semiautomatically on elements, parts and components of a machine for packaging products, for example drugs, placed inside an aseptic and/or sterile environment, to which the following description will make explicit reference without thereby losing general applicability.

In the pharmaceutical and biotechnological industries there is often a requirement for product packaging processes to use sterile materials and in sterile environments in order to prevent the products suffering particle and bacteriological contamination, i.e. contamination due to the presence in the air of solid suspended particles such as ashes, dust, spores and microorganisms.

For this purpose, the production systems comprise packaging machines or lines inserted inside cleanrooms, which separate an internal processing environment, in fact a sterile processing environment, from a surrounding non-sterile external environment, or environment having a different class of sterility or contamination. The degree of contamination of an environment is defined by the number of polluting particles present in a unit volume of air. Standard tables define contamination classes for each of which there is defined the maximum permissible number of polluting particles of the indicated dimension per cubic foot (US FED STD 209 Cleanroom standards) or per cubic metre of air (ISO 14644-1 Cleanroom standards).

The contamination class required in the process environment is a function of the product to be packaged. For example, for pharmaceutical products to be administered parenterally or nasally, or ophthalmic products, packaging in a class ISO 5 (ISO 14644-1) or class 100 (US FED STD 209) environment is required.

The separation and insulation between the two environments in some applications also aims to prevent the dispersal into the external environment of products that are potentially toxic and harmful to human health.

The asepsis and/or sterility of the processing environment is ensured by the cleanliness and sterility of each component and element contained inside the cleanroom, and by the presence of a suitable one-way flow of sterile air filtered by suitable absolute (HEPA) filters. The one-way air flow consists of threads of sterile air that move in the same direction almost parallel to one another, at substantially the same speed, in such a way as to create an even air current without turbulence. The air flow descending from top to bottom forms a front of sterile air that drags away any contaminating particles present and prevents them from rising again from the bottom of the chamber.

Inside the cleanroom there is provided the entrance for the operators assigned to performing a plurality of interventions on the packaging machine, such as, for example, adjustments, assembly and dismantling of parts and operating units, interventions that in all cases must not connect the sterile processing environment with non-sterile zones of the machine such as spaces containing mechanisms and movement mechanism.

The objective is to perform operations and interventions on the machine without compromising the sterility of the sterile environment and without contaminating previously sterilised parts and components mounted or to be mounted on the machine, in order to avoid procedures of restoring sterility that are laborious, long and very costly.

For this purpose, in order to avoid the contamination of the sterile environment, and above all of the parts with which they come into contact, the operators wear suitable protective overalls that cover all parts of their body.

In order to sterilize appropriately any object to be introduced into the cleanroom, there is provided an autoclave, provided with two hatches, which are respectively in communication with the external non-sterile environment and with the internal environment of the cleanroom, in such a way as to prevent a direct connection between said environments.

In this way the operator is able to introduce inside the cleanroom elements to be mounted onto the machine, typically standard components, operating units and devices, for example product batching or container capping devices, to be replaced at the end of production.

These parts are transferred manually by one or more operators from the autoclave to the machine on which they are mounted.

Recently however, the need has arisen to limit the intervention by operators to prevent them interacting directly with parts intended to come into contact with the product to be packaged, such as, for example, batching devices, components for introducing and supplying the product.

In fact, it has been observed that although operators are provided with protective gloves and overalls, they constitute a potential source of particle contamination.

The close proximity and the contact of said operators with sterile objects may cause the latter to be contaminated.

This possible and potential contamination may be considered to be unacceptable in certain packaging processes.

From this there arises the need to proceed with further sterilising processes after each operation and/or intervention on parts and components of the machine that are apt to come into contact with the product, with a consequent increase in the cost and time required to set up the operating system.

At the end of production it is generally necessary to dismantle the parts, the components and the operating units of the machine that have come into contact with the product or have a size that is not compatible with the next production batch. These elements have to be transferred outside the clean room to be cleaned, washed and then sterilised, to make them suitable for subsequent use.

The transfer outside the cleanroom occurs through a communicating chamber provided, similarly to the autoclave, with a first door giving access to the cleanroom and with a second door giving access to the non-sterile external environment. In this way the operators in the cleanroom transfer the elements dismantled from the machine to the chamber from which, after the first door has been closed hermetically, other operators remove them to subject them to washing and sterilising operations.

These manual procedures nevertheless have the drawback of forcing the operators to touch parts and components of the machine on which the packaged product is present in more or less great quantities. Also in the case of pharmaceutical products that are not particularly hazardous and harmful—such as cytotoxic products for which special procedures and containing systems are provided—this direct, prolonged and repeated contact with pharmaceuticals should be avoided as it exposes the operators to the possible absorption of unspecified quantities of product that may harm the health or cause health complaints of varying gravity. This is particularly true in the case of products in the form of fine powders, which can be easily diffused in the air and thus be inhaled and/or absorbed by the operators.

In order to overcome this problem it is currently necessary to limit the operating time of each operator, i.e. the time during which the latter is in contact with parts touched by the product. This is achieved through a frequent turnover of operators, which requires an appropriate number of operators to be made available and prepared for operations inside the cleanroom, with a consequent increase in system running costs.

Alternatively, it is necessary to provide the operators with particular equipment, such as completely airtight overalls and masks that are able to insulate the operators completely from the surrounding environment. In addition to being very costly, this equipment places significant limitations on movements and performable manual operations.

SUMMARY OF THE INVENTION

An object of the present invention is to improve known apparatuses and methods for handling and treating elements of a packaging machine operating in a sterile-atmosphere environment.

Another object is to devise a system and a method that enable elements, parts, components and operating units of a packaging machine to be handled and conveyed within a sterile environment atmosphere, without requiring a direct manual intervention by operators.

A further object is to obtain a system and a method that enable parts, components and operating units to be assembled on or dismantled from a packaging machine automatically without a direct manual intervention by operators.

Still another object is to devise a system and a method preventing the operators coming into direct contact with parts of the machine on which there is product to be packaged.

In a first aspect of the invention there is provided a system for transferring and moving elements that are removably associable with a packaging machine comprising at least a transferring unit provided with a movement arrangement that is suitable for receiving and supporting said elements, said movement arrangement being movable for transferring to and/or removing said elements from said machine.

Owing to this aspect of the invention it is possible to supply a system that enables elements of a packaging machine such as parts, components, operating units to be transferred and moved, without requiring direct manual intervention by operators. In particular, thanks to the transferring unit it is possible to assemble on the packaging machine or dismantle therefrom a plurality of diverse elements automatically, without the operators coming into direct contact with the elements. This is particular advantageous if the machine is placed inside a cleanroom. In this case, direct contact of the operator both with sterile elements to be installed on the machine, and with elements soiled with product to be dismantled from the machine at the end of production is in fact not advisable and is sometimes not acceptable. In the first case the system enables the elements to be maintained at the same level of sterility (contamination class) that they possess exiting from an autoclave.

In the second case the system preserves the operators from contact with the product and prevents possible absorption of unspecified quantities of said product, that may harm the health of or cause health complaints in operators.

In a second aspect of the invention there is provided a method for transferring and moving elements that are removably associable with a packaging machine wherein there is provided supporting and conveying said elements by means of at least a transferring unit and transferring to and/or removing from said packaging machine said elements using a movement arrangement of said transferring unit.

BRIEF DESCRIPTION OF THE DRAWINGS

The invention can be better understood and implemented with reference to the attached drawings, which illustrate a preferred embodiment by way of non-limiting example, in which:

FIG. 5 is a partial enlarged view of FIG. 4, showing a first element partially connected to a supporting arrangement of the packaging machine;

FIG. 6 is a partial enlarged view in FIG. 1, showing the transferring unit associated with a washing unit in a connecting position, the second connecting position being represented by a broken line.

DETAILED DESCRIPTION OF THE INVENTION

With reference to FIGS. 1 to 6, there is generally illustrated a system 1 for transferring and moving elements 50, 60 for an automatic packaging machine 3 operating inside a controlled-atmosphere processing chamber 2.

The elements 50, 60 comprise parts, components, operating units and devices of said machine 3, consisting for example of a batching/capping machine configured for batching a pharmaceutical product inside containers (not shown) and for capping the latter.

Figure 1:
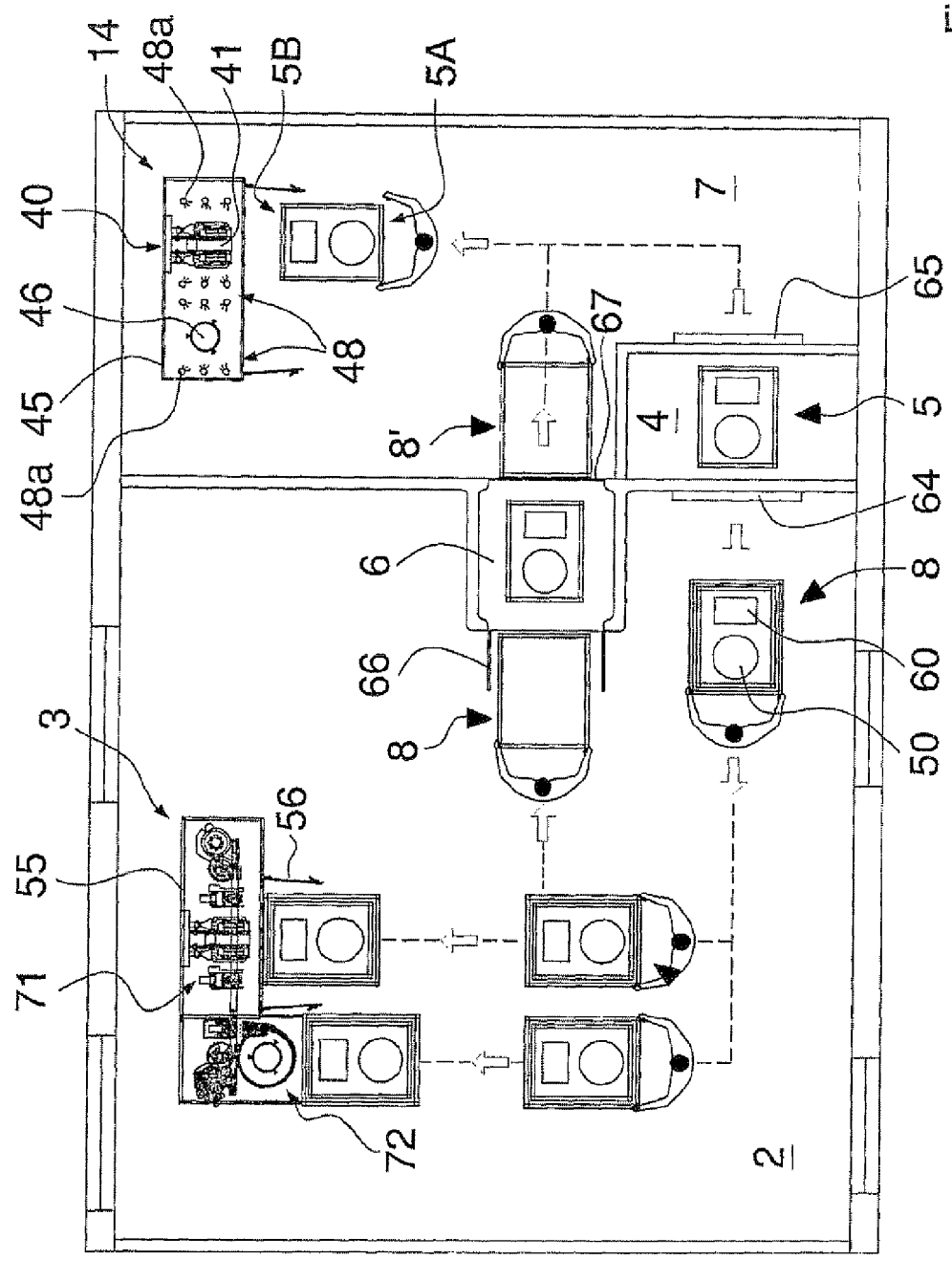
FIG. 1 is a schematic plan view of a system for handling and treating elements of a packaging machine according to the invention, showing in particular a packaging machine inside a processing chamber and a transferring unit arranged in different, successive operating positions.

According to what has been illustrated in FIG. 1, the processing chamber 2 is a cleanroom of the type normally used in pharmaceutical production, i.e. insulated from the external environment by means of airtight walls and doors, and bounding a sterile environment, subject to a flow of vertical one-way sterile air, generated by known air treatment and a conditioning device that is not shown.

The chamber 2 is provided with at least a communication chamber 6, a so-called transferring bush, which connects said chamber 2 to a service room 7 that has a non-controlled atmosphere or anyway a contamination class that is less or more approximate that that of the processing chamber 2.

The aforesaid communication chamber 6 is provided with a first access door 66 to the inside of the chamber 2 and with a second access door 67 to the service room 7. Using these two doors prevents a direct connection between the inside of the chamber 2 and the service room 7, in order to maintain the integrity of the sterile atmosphere inside the chamber 2. The communication chamber 6 is also subject to a one-way sterile air flow to adapt the atmosphere within to that of the chamber 2, during opening of the first door 66.

The system 1 further comprises a sterilising arrangement 4 comprising one or more autoclaves, of known type, suitable for sterilising elements 50, 60 to be introduced into said processing chamber 2. Similarly to the communication chamber 6, also the autoclave 4 is provided with an internal access hatch 64 and an external access hatch 65, suitable for making the autoclave 4 communicate respectively with the chamber 2 and with the service room 7.

The system 1 further comprises at least a transferring unit 5 that is movable and arranged for conveying a plurality of elements 50, 60 from the service room 7 to the packaging machine 3, through the autoclave 4, and from the packaging machine 3 to the service room 7, through the communication chamber 6.

The transferring unit 5 is, in fact, arranged for being sterilised inside the autoclave 4 together with the elements 50, 60 contained therein. For this purpose, the transferring unit 5 and the elements 50, 60 are made of materials that are suitable for withstanding sterilisation temperatures and pressures.

Figure 2:
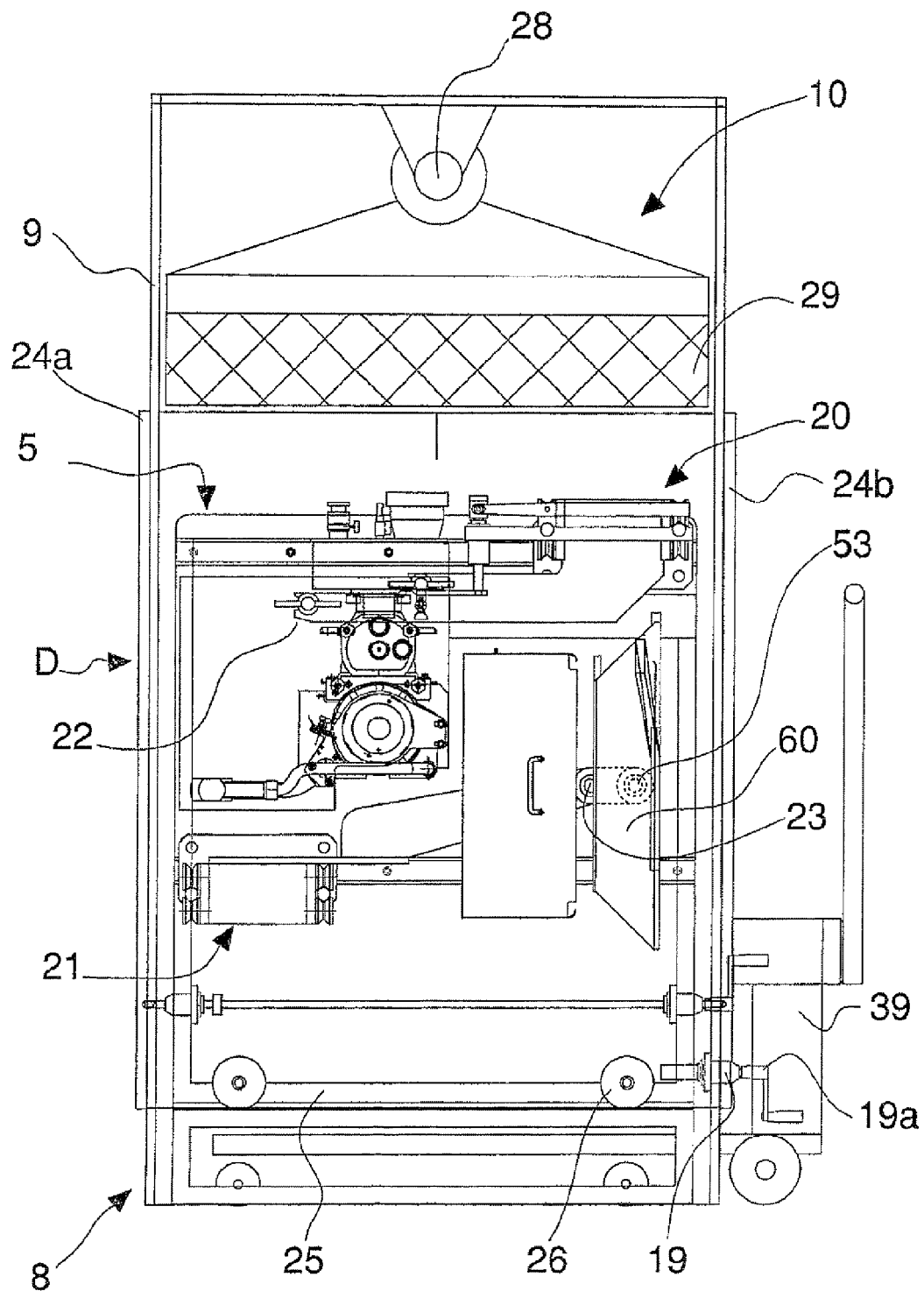
FIG. 2 is a schematic and enlarged side view of a transferring unit of the system of FIG. 1 in association with a carriage.

According to what has been illustrated in FIG. 2, the transferring unit 5 comprises a movement arrangement 20, 21 that is movable and arranged for supporting and moving respective elements 50, 60 to be mounted on or dismantled from the packaging machine 3. In particular the movement arrangement 20, 21 is movable between a first operating position D in which it is arranged inside said transferring unit 5 and a second operating position E (FIG. 3) in which it partially protrudes outside said transferring unit, for example for removing and/or transferring elements 50, 60.

The movement arrangement 20, 21 comprises respective grasping arrangement 22, 23 suitable for hooking attaching portions 51, 61 of the elements 50, 60.

Figure 3:
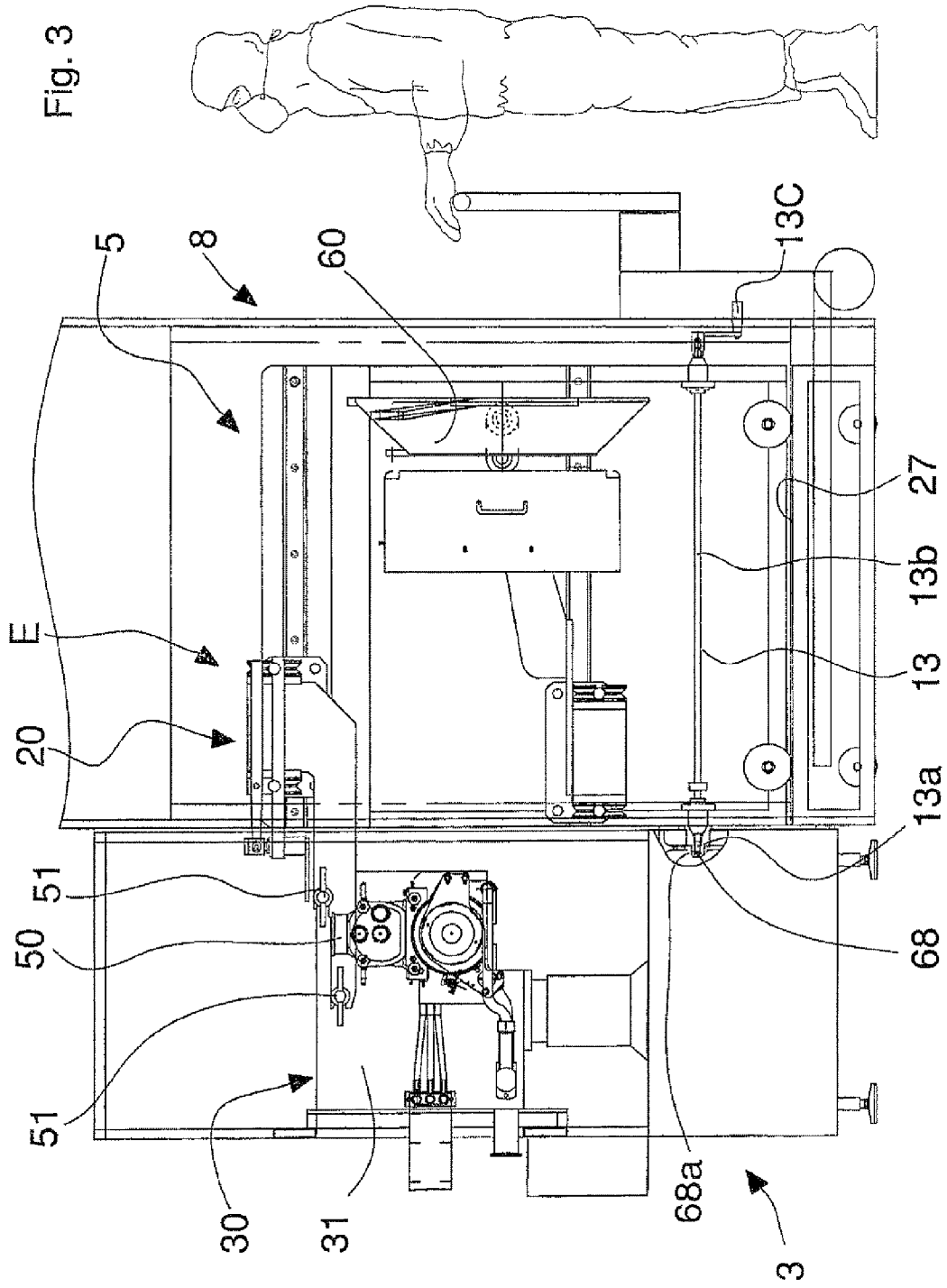
FIG. 3 is a schematic lateral view of the transferring unit associated with the packaging machine in FIG. 1, in an operating step.
Figure 4:
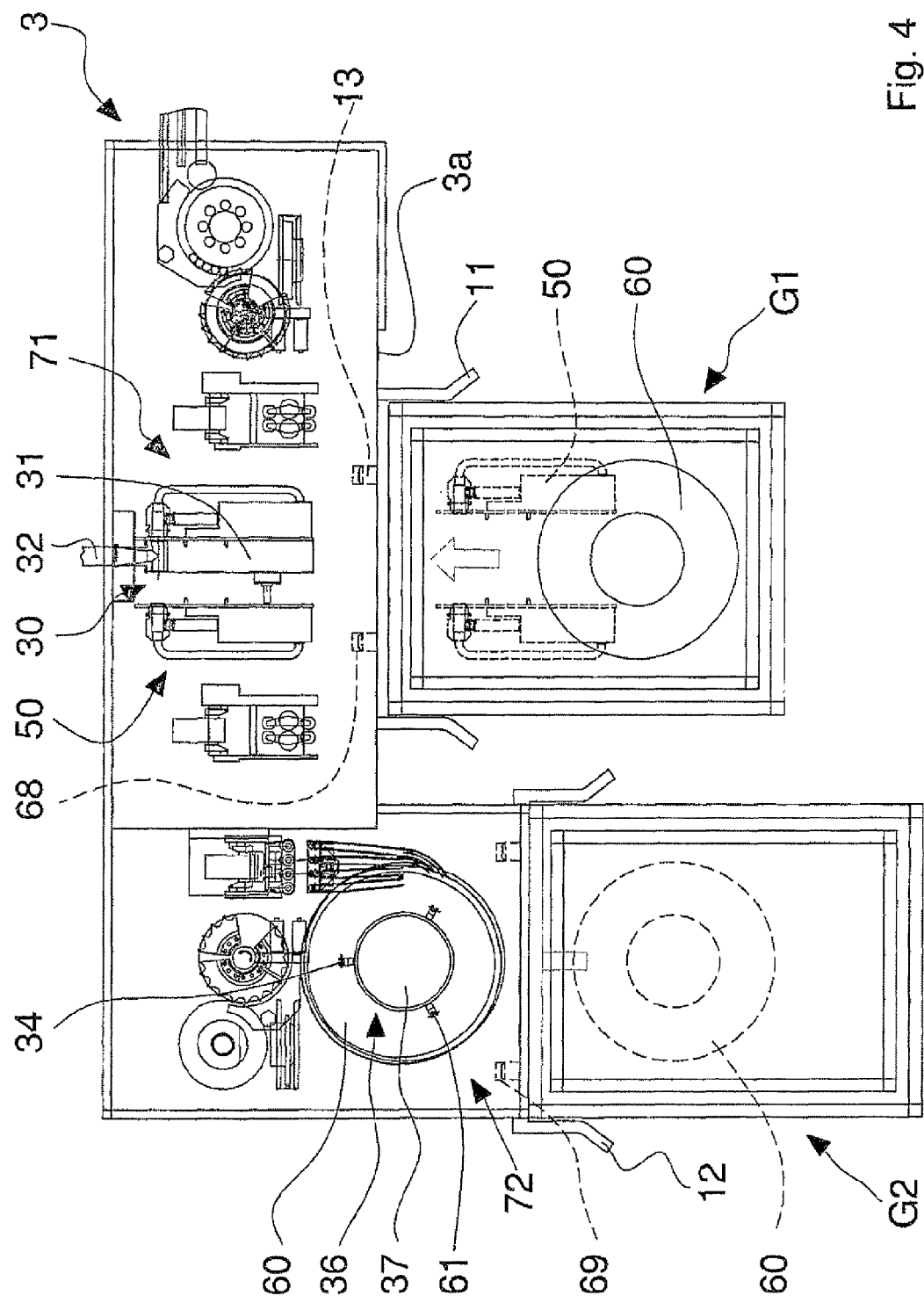
FIG. 4 is a plan view of the transferring unit and of the packaging machine, showing said transferring unit in a hooking position on said machine, a second hooking position being represented by a broken line.

According to what has been illustrated in FIGS. 2, 3 and 4, the movement arrangement 20, 21 is driven manually by the operator by means of respective controls such as cranks or handwheels. Instead of the latter, a portable driving device, for example electric screwdrivers can be used. In an embodiment that is not shown, the movement arrangement 20, 21 is driven by motors and/or actuators that are removably mounted on the transferring unit 5, in such a way as to be able to be dismantled during the washing and sterilisation steps in the autoclave.

Alternatively, said motor is suitably configured and insulated for withstanding washing agents and sterilisation pressures and temperatures.

The transferring unit 5 further comprises a supporting frame 25 to which said movement arrangement 20, 21 is slidably fixed.

The frame 25 is provided with wheels 26 for enabling the unit 5 to be moved.

In particular, the wheels enable said transferring unit 5 to be easily inserted into and/or extracted form the sterilising arrangement 4 and/or from the communication chamber 6.

Although the atmosphere inside the chamber 4 is sterile and is of a contamination class that is appropriate to the type of process to be conducted, the floor of said chamber 4 can be considered to be of a lower or more approximate contamination class as on it or near it, owing to the one-way vertical air flow, the polluting solid particles that may be present within the chamber are distributed and remain confined.

Thus in order to prevent the transferring unit 5 at the outlet of the autoclave 4 coming into direct contact with the aforesaid floor there is provided a carriage 8 arranged for housing and supporting the transferring unit 5 inside the processing chamber 2.

According to what has been illustrated in FIG. 3, the carriage 8 has a supporting plane 27 that is arranged at the same position or height as the bottom surface of the autoclave 4 and of the communication chamber 6 to enable the transferring unit 5 to be inserted into and/or withdrawn from the transferring unit 5.

A removal arrangement 19, fixed to the carriage 8 (FIG. 2), is provided for hooking and dragging the aforesaid transferring unit 5 onto the carriage 8 or for pushing it outside the carriage 8.

The removal arrangement 19 comprises, for example, a telescopic arm or pantograph mechanism, which is able to be lengthened and shortened and is provided with a free end that is suitable for grasping a portion of the supporting frame 25 of the transferring unit 5. The removal arrangement 19 can be driven manually by an operator by means of a crank or handwheel 19a, or using an electric screwdriver.

According to what is visible in FIG. 2, the carriage 8 is further provided with a containing element 9 suitable for making a covering structure that is able to enclose completely the transferring unit 5. The containing element 9 is substantially box-shaped and comprises two closed side walls, the remaining two opposite walls being provided with respective movable doors 24a, 24b for the entry and exit of the transferring unit 5.

A conditioning device 10 is provided in the upper portion of the containing element 9 to generate a one-way vertical air flow, from top to bottom. The conditioning device 10 comprises one or more fans or blowers 28 able to suck sterile air from the processing chamber and direct it through a filtering arrangement 29, for example HEPA absolute filters, onto the transferring unit 5.

In order to facilitate moving the carriage 8, a possibly motor-driven transpallet 39 can be used that is able to lift and move the carriage 8 and the transferring unit 5.

In an embodiment that is not shown, it is further provided that the carriage 8 is provided with a driving device and with a controlling device configured for moving the aforesaid carriage 8 independently and automatically, without the assistance of operators, according to set trajectories and paths. The carriage 8 may comprise, for example, an AGV (Automated Guided Vehicle) unit of known type that is movable along magnetic tracks obtained in the floor of the processing chamber 2 or guided by radio-type navigation systems or GPS.

According to what has been illustrated in FIG. 4, the packaging machine 3 comprises a centring arrangement 11, 12 that enables the carriage 8, i.e. the transferring unit 5, to be placed in one or more hooking positions with respect to the machine 3.

There are, for example, two hooking positions (FIG. 4) corresponding to respective specific operating zones of the machine 3, respectively a first operating zone 71 in which there has to be assembled a first element 50, and a second operating zone 72, in which a second element 60 has to be mounted.

The centring arrangement 11, 12 may comprise, for example, one or more pairs of prongs or elongated elements, typically a first pair of prongs 11 and a second pair of prongs 12, each of which is fixed orthogonally to a lower front portion 3a of the machine 3, at the respective operating zone 71, 72.

The prongs of each pair 11, 12 are spaced apart from one another and divergent to the exterior of the machine 3 in such a way as to abut lower side walls of the carriage 8 and progressively guide and centre the latter, pushed to the machine 3, in a defined respective hooking position G1, G2.

In each hooking position G1, G2 the transferring unit 5 is removably locked on the machine 3 through a joining arrangement 13 configured for engaging in respective attaching arrangement 68, 69 provided in said lower front portion of the machine 3, at the centring arrangement 11, 12. In particular, the machine 3 comprises a first attaching arrangement 68, associated with the first pair of prongs 11 and a second attaching arrangement 69, associated with the second pair of prongs 12.

The joining arrangement 13 comprises, for example, a pair of parallel and spaced pins 13a (FIG. 3) that are rotatably connected to the supporting frame 25 of the transferring unit 5 and provided with external threading. The pins 13a are arranged for being inserted and screwed into in respective threaded seats 68a, 69a (only the seat 68a of which is illustrated in FIG. 3) of the respective attaching arrangement 68, 69.

The joining arrangement 13, i.e. the pins 13a, can be rotated manually by the operator using respective rods 13b controlled by cranks 13c or by portable driving device, for example electric screwdrivers.

It is further provided in an embodiment that is not shown that the joining arrangement 13 is fixed to the carriage 8 to lock the latter on the machine 3. In this case, the removal arrangement 19 maintains the transferring unit 5 fixed to the carriage 8.

According to what has been illustrated in FIGS. 3, 4 and 5, a supporting arrangement 30, 36 is provided on the machine 3 to enable respective elements 50, 60 to be mounted and dismantled that are conveyed by the transferring unit 5.

The supporting arrangement 30, 36 comprises respective supporting elements 31, 37 fixed to a horizontal plane and/or to a vertical plane of the machine 3 and is provided with respective hooking elements 33, 34 (FIG. 5) suitable for fixing and supporting the elements 50, 60.

The supporting arrangement 30, 36 further comprises a connecting device 32 for connecting to electric, pneumatic, fluid, product supply circuits of the machine, circuits for dispatching and receiving electric or optical signals to/from sensors and a coupling member 35 for connection to kinematic and movement mechanisms of the machine.

Specifically, with reference to the packaging machine illustrated in FIGS. 1 to 6, a first supporting arrangement 30 is arranged for receiving and supporting a first element 50, consisting for example in an operating unit for batching a powder product in containers and consisting of two parts.

The first supporting arrangement 30 comprises a first supporting element 31 fixed to a horizontal plane of the machine 3 and provided with a first hooking element 33 suitable for abutting on and locking an abutting element 52 of the operating unit 50. The hooking elements are, for example, shaped seats 33 suitable for receiving respective locking pins 52. There is provided a connecting device 32 for connecting to a pneumatic and product supply circuit of the machine and a coupling member 35, consisting of a motor-driven pin connected to the motor of the machine to drive mechanical devices of the operating unit 50.

A second supporting arrangement 36 is on the other hand provided for receiving and supporting a second element 60, consisting for example of a vibrating supply device for caps closing containers. The second supporting arrangement 36 comprises a second supporting element 37 fixed to a horizontal plane of the machine 3 on which the aforesaid device 60 is locked. A second hooking element 34 locks the second element 60 to the second supporting element 37.

The system 1 comprises inside the service room 7 a washing unit 14 (FIGS. 1 and 6) configured for washing the elements 50, 60 internally and externally.

Typically said elements comprise operating units, parts and components that have come into contact with the product, which, dismantled from the machine at the end of production, need to be cleaned and washed.

The elements are transferred from the packaging machine 3 to the washing unit 14 using the transferring unit 5 according to operating procedures that will be disclosed in detail in the continuation of the description.

According to what has been better illustrated in FIG. 1, inside the service room 7 there can be provided a further carriage 8' that is identical to the carriage 8 operating inside the processing chamber 2 and arranged for receiving the transferring unit 5 at the outlet of the communication chamber 6.

The transferring unit 5, possibly contained inside said further carriage 8', is moved by an operator and made to abut on the washing unit 14.

Similarly to what happens with the packaging machine 3, the transferring unit 5 is positioned with respect to the washing unit 14 in one of different connecting positions, by means of respective centring arrangement 81, 82 provided on said washing unit 14 and substantially identical to the centring arrangement 11, 12 of the packaging machine 3 (FIG. 6).

In each connecting position the transferring unit 5 is removably locked on the washing unit 14 as the joining arrangement 13 of said unit 5 is able to engage a respective attaching arrangement 83, 84 provided on a lower front portion of said washing unit 14, at the further centring arrangement 81, 82. The further attaching arrangement 83, 84 of the washing unit 14 is almost identical to the attaching arrangement 68, 69 of the packaging machine 3.

With particular reference to FIG. 6, the connecting positions of the transferring unit to the washing unit 14 may, for example, be two: a first connecting position L1 for transferring the first element 50 to the washing unit 14, and a second connecting position L2 for transferring the second element 60.

The washing unit 14 includes a protecting cover 45, provided with one or more doors and defining an internal washing space 49, and a resting arrangement 40, 46 that is substantially identical to the supporting arrangement 30, 36 of the packaging machine 3 as it is configured for enable the respective elements 50, 60 mounted on the machine 3 to be mounted and dismantled.

The resting arrangement 40, 46 comprises respective supporting elements 41, 47 fixed to a plane of the washing unit 14 and provided with respective hooking arrangement 43, 44 suitable for hooking and supporting the elements 50, 60.

Unlike the supporting arrangement 30, 36, the resting arrangement 40, 46 may comprise attachments and connections suitable for conveying washing fluids inside the elements 50, 60.

With particular reference to FIG. 6, the washing unit 14 is arranged for receiving the first element 50, which can be fixed to a first resting arrangement 40, and the second element 60, which can, on the other hand, be fixed to the second resting arrangement 46.

The first element 50 is a batching unit that is fixed to first resting arrangement 40 in such a way that a supply device 42 of the washing unit 14, consisting of suitable connections, is able to deliver washing fluids into conduits, pipes and internal passages of said operating unit 50 for internal washing and cleaning.

The washing unit 14 is further provided with a dispensing arrangement 48, arranged in the internal washing space 49 for externally washing the operating unit 50. The dispensing arrangement 48 comprises, for example, a plurality of sprayers or nozzles 48a distributed in the internal washing space 49 to sprinkle and spray external surfaces of the elements 50, 60.

In an embodiment of the system that is not illustrated, there is provided a further washing unit intended for automatically washing, without the manual intervention of operators, the transferring unit 5, in order to eliminate from the supporting frame and from the movement arrangement 20, 21 possible traces and residue of product that have become detached from the conveyed elements 50, 60.

The operation of the system 1 substantially provides a first sequence of operating steps preparatory to production, i.e. to operation of the packaging machine 3, and a second sequence of steps to be conducted at the end of production.

Initially, the washed and sterilised operating elements 50, 60 have to be mounted and assembled on the packaging machine 3 placed inside the controlled-atmosphere processing chamber 2.

The elements 50, 60 cleaned and washed in the service room 7 are arranged there on a transferring unit 5.

The transferring unit 5 and the elements 50, 60 present therein are then introduced inside the autoclave 4, where they are sterilised.

At the end of the sterilising step, an operator opens the internal access hatch 64 of the autoclave 4 and arranges the carriage 8 that is suitable for receiving and containing the transferring unit 5. The operator acts on the removal arrangement 19 that hooks and drags the transferring unit 5 inside the carriage 8.

The conditioning device 10 of the carriage 8 is working to direct a one-way vertical air flow, from top to bottom, on the unit 5 and maintain the atmosphere inside the containing element 9 of the carriage 8 in slightly excess pressure with respect to the chamber 2, in order to prevent the entry of possible contaminating solid particles.

When one of the movable doors 24a, 24b of the containing element 9 is open, the operator acts on the carriage 8, for example for driving the removal arrangement 19, always being arranged on the side opposite said open door, in such a way that possible polluting particles released thereby do not penetrate inside the containing element.

Before making the carriage 8 approach the machine 3, the operator opens the door 24a, 24b of the wall facing said machine, whilst corresponding doors 56 of a protective structure 55 of the machine 3 have been opened beforehand (FIG. 1).

If the first operating element 50 has to be mounted on the machine 3 the operator makes the carriage 8 approach in such a way that the first centring arrangement 11 precisely positions the carriage 8 at the first operating zone 71 of the machine 3.

After positioning, the operator drives the joining arrangement 13 in such a way as to lock the transferring unit 5 on the machine 3 in the first hooking position G1.

It is thus possible to drive the first movement arrangement 20 of the transferring unit 5 to locate the first element 50 on the first supporting arrangement 30. In particular, the first movement arrangement 20 transfers the first element 50 to the first supporting element 31 of the first supporting arrangement 30, making the locking pins 52 of the operating unit 50 engage the hooking element 33. At the same time, the element 50 is coupled with the connections 32 for connecting to the various supply circuits of the machine and to the mechanical power points 35.

After completing mounting of the first element 50, the transferring unit 5 can be released from the machine 3 disengaging the joining arrangement 13 from the first attaching arrangement 68. At this point the carriage 8 can be distanced from the machine 3 and, if necessary, moved to the second operating zone 72 of the machine 3 for mounting the second element 60.

The transferring unit is then locked by the joining arrangement 13 onto the machine 3 in the second hooking position G2 and the second movement arrangement 21 is driven to position the second element 60 on the second supporting element 37.

The aforesaid operations are repeated for the plurality of elements present on the transferring unit 5 that have to be mounted on the machine.

When the operations have been completed the packaging machine 3 is ready for production.

The same sequence of steps necessary for mounting the elements 50, 60 on the machine 3 can be used in reverse order to dismantle and load onto the transferring unit 5 the elements 50, 60 to be conveyed outside the processing chamber 2. In this case, the movement arrangement 20, 21 will hook and extract the elements 50, 60 from the respective supporting arrangement 30, 36.

During movement through the processing chamber 2, the containing element 9 of the carriage 8 prevents particles and product residue present on the elements 50, 60 from being able to disperse in the chamber 2 and, in particular, come into contact with the operator working on the carriage 8.

The carriage 8 is then taken to the communication chamber 6, the first access door 66 of which to the chamber 2 is open, the second passage door 67, to the service room 7, being hermetically sealed.

The removal arrangement 19 is driven to push the transferring unit 5 inside the communication chamber 6. The latter, similarly to the autoclave 4, has a bottom surface placed almost at the same level as the supporting plane 27 of the carriage 8 to enable the transferring unit 5 to be moved.

During the various operating steps disclosed above one or more operators move manually the carriage 8 and drive manually the various operating arrangement 19, 13, 20, 21 of the transferring unit 5 and of the carriage 8.

The transferring unit 5 and the carriage 8 can anyway comprise a driving device and a controlling device that are of known type that is not shown, configured for moving the aforesaid carriage 8 and driving the various operating arrangement independently and automatically, without requiring the help or the presence of operators inside the processing chamber 2.

Once the transferring unit has been introduced inside the autoclave 4 and the first door 66 has been closed, it is possible to open the second door 67 of the space to enable an operator to remove the transferring unit 5.

A tilted ramp will be provided to enable exit from the communication chamber 6 if the floor of the service room 7 is at a different level, for example a lower level than the bottom surface of said space 6.

Alternatively, there can be provided a further carriage 8' that is able to remove the transferring unit 5, using the same operating procedures and sequences used to extract said unit 5 from the autoclave 4.

The transferring unit 5 is moved by the operator until it abuts on the washing unit 14 in respect to which it is positioned and locked in sequence in the provided connecting positions L1, L2.

Similarly to what occurs with the carriage 8 inside the processing chamber 2, the operator interacts with the transferring unit 5 arranging himself at a respective rear side 5A opposite a front access side 5B (FIG. 1) inside the transferring unit 5. This prevents the operator from coming into contact with residues of product present on the elements 50, 60 conveyed by the transferring unit 5.

In the first connecting position L1, the first movement arrangement 20 of the transferring unit 5 transfers and mounts the first element 50 on the first resting arrangement 40 of the washing unit 14. This mounting further involves connecting conduits, pipes and internal passages present in the first element to the attachments and connections 47 provided in the first resting arrangement 40 for delivering washing fluids.

In the second connecting position L2 the second movement arrangement 21 moves and mounts the second element 60 on the second resting arrangement 46. In this case, as the second element 60 is not provided with conduits and internal passages, the presence on the second resting arrangement 46 of specific connections and attachments for the dispensing of washing fluids is not required.

Obviously, the washing unit 14 can be configured in function of the elements to be washed and thus comprise further resting arrangement suitably arranged for receiving and supporting respective elements, provided or not provided with connections and attachments for the internal washing of said elements.

Once the elements have been assembled on the washing unit 14, the corresponding protecting cover 45 can be closed and the external and internal washing cycle can be started.

The method, duration and features of the internal and external washing are defined in function of the type of package product, the form and structure of the elements, required cleaning requirements, etc.

At the end of washing, the operating elements 50, 60 can be dismantled from the washing unit 14 using the transferring unit 5 or manually by the operators.

In the first case, the elements 50, 60 have been washed suitably and in compliance with required cleaning requirements and can be conveyed together with the transferring unit 5 inside the autoclave 4 for sterilisation. The transferring unit 5, before removing the elements, has been cleaned and washed beforehand, in such a way as to eliminate traces and residues of product that may be present on the supporting frame 25, on the movement arrangement 20, 21 and on the grasping arrangement 22, 23. The transferring unit 5 can be washed manually by the operators or automatically using a respective and specific washing unit.

If the washing performed by the washing unit 14 is insufficient or if the elements 50, 60 have to be dismantled for modifications, adjustments, or repairs they have to be handled by the operators. Nevertheless, this handling in this step is safe, as most of the product present on the elements 50, 60 was eliminated during automatic cleaning in the washing unit 14.

At the end of these manual operations, the elements 50, 60 can be positioned on the transferring unit 5 and then placed in the autoclave 4 for sterilising.

It should be observed that the system that is the object of the present invention enables elements of a packaging machine to be transferred and moved semiautomatically or automatically without requiring direct manual intervention on said elements by operators.

This is particularly important both during the mounting step to prevent possible contamination of the washed and sterilised elements, and during the dismantling step to prevent the operator coming into contact with the packaged product.

In an embodiment of the system, all the operating procedures can be performed automatically without requiring the presence of operators inside the processing chamber 2.

It is clear that the system 1 may comprise inside the processing chamber 2 a plurality of packaging machines 3, operating independently on distinct production lines or in series, connected together to form a complete packaging line.

Similarly, in the system 1 a plurality of transferring units 5 and of respective carriage 8 can be used to transfer, mount and dismantle at the same time a plurality of elements and thereby reduce operating time.

The invention claimed is:

1. System for transferring and moving elements removably associable with a packaging machine, comprising:
at least a transferring unit provided with a movement arrangement that are suitable for receiving and supporting said elements, said movement arrangement being movable for transferring to and/or removing said elements from said packaging machine;
a processing chamber suitable for containing said packaging machine and said transferring unit; said chamber being insulated and having a controlled atmosphere; and
a service room adjacent said processing chamber and connected to said processing chamber through a communication chamber; said communication chamber comprising a first access door to said chamber and a second access door to said service room.

2. System according to claim 1, wherein said transferring unit comprises a supporting frame provided with wheels and suitable for slidably supporting said movement arrangement.

3. System according to claim 2, wherein said movement arrangement is driven by an actuating device connected to said supporting frame.

4. System according to claim 1, wherein said movement arrangement comprises respective grasping arrangement arranged for hooking attaching portions of said elements.

5. System according to claim 1, wherein said movement arrangement is movable between a first operating position wherein said movement arrangement is arranged inside said transferring unit and a second operating position wherein said movement arrangement is extended for removing and/or transferring said elements.

6. System according to claim 1, wherein said movement arrangement is drivable manually by an operator.

7. System according to claim 1, wherein said transferring unit comprises a joining arrangement arranged for engaging an attaching arrangement of said packaging machine to removably lock said transferring unit to said packaging machine.

8. System according to claim 1, comprising a carriage suitable for supporting and conveying said transferring unit.

9. System according to claim 8, wherein said carriage comprises a containing element arranged for enclosing said transferring unit.

10. System according to claim 9, wherein said carriage comprises a conditioning device arranged in an upper portion of said containing element and suitable for generating a substantially vertical one-way air flow inside said containing element.

11. System according to claim 10, wherein said conditioning device comprises a fan and a filtering arrangement.

12. System according to claim 8, wherein said carriage is movable manually by an operator or by means of a driven carriage.

13. System according to claim 8, wherein said carriage comprises a driving device and a controlling device suitable for automatically moving said carriage along set trajectories and paths.

14. System according to claim 8, wherein said carriage comprises removal arrangement suitable for hooking and locking said transferring unit, said removal arrangement being further movable for introducing and/or ejecting said transferring unit into and/or from said carriage.

15. System according to claim 8, wherein said transferring unit comprises a joining arrangement arranged for engaging an attaching arrangement of said packaging machine to removably lock said transferring unit to said packaging machine and said carriage comprises joining arrangement arranged for engaging in attaching arrangement of said machine to removably lock said carriage to said packaging machine; supporting arrangement comprising hooking elements suitable for abutting on and locking abutting elements of said elements.

16. System according to claim 15, wherein said supporting arrangement comprises connecting device for connecting said elements to circuits of the machine.

17. System according to claim 1, wherein said chamber comprises a device for generating a controlled one-way air flow.

18. System according to claim 1, wherein said communication chamber comprises a device for generating a controlled one-way air flow inside said communication chamber.

19. System according to claim 1, comprising a sterilising arrangement configured for housing and containing said transferring unit.

20. System according to claim 19, wherein said sterilising arrangement comprises an autoclave provided with an internal access hatch giving access to said processing chamber and an external access hatch giving access to said the service room.

21. System according to claim 1, wherein said elements and said transferring unit are sterilisable in an autoclave.

22. System according to claim 1, comprising at least a washing unit suitable for washing said elements internally and/or externally.

23. System according to claim 22, wherein said washing unit is placed in said service room.

24. System according to claim 22, wherein said washing unit comprises a protecting cover, provided with one or more doors and defining an internal washing space.

25. System according to claim 24, wherein said washing unit comprises a resting arrangement suitable for supporting said elements during a washing step, said resting arrangement being further configured for receiving said elements from and giving said elements to said movement arrangement of said transferring unit.

26. System according to claim 25, wherein said washing unit comprises a supply device suitable for being connected to said elements to deliver washing fluids inside the washing unit.

27. System according to claim 24, wherein said washing unit comprises a dispensing arrangement, arranged inside said internal washing space for spraying a washing fluid onto said elements.

28. System according to claim 27, wherein said dispensing arrangement comprises a plurality of sprayers or nozzles.

29. System according to claim 22, wherein said washing unit comprises respective centring arrangement suitable for defining at least a connecting position of said transferring unit to said washing unit.

30. System according to claim 29, wherein said respective centring arrangement of said washing unit comprises at least a pair of elongated elements, spaced from one another and substantially parallel, fixed substantially orthogonally to said washing unit.

31. System according to claim 29, wherein said transferring unit comprises joining arrangement arranged for engaging attaching arrangement of said packaging machine to removably lock said transferring unit to said packaging machine and said washing unit comprises attaching arrangement suitable for being engaged by said joining arrangement of said transferring unit for locking the transferring unit on said washing unit in said connecting position.

32. System according to claim 1, wherein said controlled atmosphere is sterile.

\* \* \* \* \*